(12) United States Patent
Connor (10) Patent No.: US 9,138,232 B2
(45) Date of Patent: Sep. 22, 2015

(54) ANEURYSM OCCLUSION BY ROTATIONAL DISPENSATION OF MASS

(75) Inventor: Robert A. Connor, Minneapolis, MN (US)

(73) Assignee: Aneuclose LLC, Forest Lake, MN (US)

( * ) Notice: Subject to any disclaimer, the term of this patent is extended or adjusted under 35 U.S.C. 154(b) by 720 days.

(21) Appl. No.: 13/068,933

(22) Filed: May 24, 2011

(65) Prior Publication Data

US 2012/0303052 A1 Nov. 29, 2012

(51) Int. Cl.
*A61M 29/00* (2006.01)
*A61B 17/12* (2006.01)

(52) U.S. Cl.
CPC ....... *A61B 17/12113* (2013.01); *A61B 17/1215* (2013.01); *A61B 17/1219* (2013.01); *A61B 17/12145* (2013.01); *A61B 17/12163* (2013.01); *A61B 17/12186* (2013.01); *A61B 17/12195* (2013.01); *A61B 2017/12054* (2013.01); *A61B 2017/12068* (2013.01)

(58) Field of Classification Search
CPC ............. A61B 17/1214; A61B 12/12145; A61B 12/1215; A61B 12/12154; A61B 2017/1205–2017/12095; A61M 2025/0042; A61M 2025/0073; A61M 25/0069–25/007; A61M 2025/1093
USPC .......... 606/108, 195, 200; 623/1.21; 128/831, 128/843; 604/533
See application file for complete search history.

(56) References Cited

U.S. PATENT DOCUMENTS

| | | |
|---|---|---|
| 5,334,210 A | 8/1994 | Gianturco |
| 5,382,259 A | 1/1995 | Phelps et al. |
| 5,522,822 A | 6/1996 | Phelps et al. |
| 5,645,559 A | 7/1997 | Hachtman et al. |
| 5,690,666 A | 11/1997 | Berenstein et al. |
| 5,700,258 A * | 12/1997 | Mirigian et al. ................. 606/1 |
| 5,718,711 A | 2/1998 | Berenstein et al. |
| 5,723,004 A | 3/1998 | Dereume et al. |
| 5,749,894 A | 5/1998 | Engelson |
| 5,766,219 A | 6/1998 | Horton |
| 5,769,882 A | 6/1998 | Fogarty et al. |
| 5,769,884 A | 6/1998 | Solovay |
| 5,861,003 A | 1/1999 | Latson et al. |
| 5,916,235 A | 6/1999 | Guglielmi |
| 5,928,260 A | 7/1999 | Chin et al. |
| 5,941,249 A | 8/1999 | Maynard |
| 5,948,018 A | 9/1999 | Dereume et al. |
| 5,951,599 A | 9/1999 | McCrory |
| 5,976,162 A | 11/1999 | Doan et al. |
| 6,024,754 A | 2/2000 | Engelson |
| 6,063,111 A | 5/2000 | Hieshima et al. |
| 6,096,034 A | 8/2000 | Kupiecki et al. |
| 6,139,564 A | 10/2000 | Teoh |
| 6,165,193 A | 12/2000 | Greene et al. |
| 6,165,212 A | 12/2000 | Dereume et al. |
| 6,168,592 B1 | 1/2001 | Kupiecki et al. |

(Continued)

*Primary Examiner* — Katherine Rodjom
*Assistant Examiner* — Jonathan Hollm (57) ABSTRACT

This invention is a device for occluding an aneurysm comprising: a rotating member that is inserted into, and then rotated within, the aneurysm; and one or more fill members that are dispensed outwards from one or more openings in the rotating member toward the aneurysm walls. Coordination of the rate of rotation of the rotating member with the rate at which the one or more fill members are dispensed from the rotating member can create a densely-packed spiraling mass that fills a higher percentage of the volume of the aneurysm interior than is possible with deployment of coils in the less-directed, relatively-random manner used in the prior art.

5 Claims, 3 Drawing Sheets

(56) References Cited

U.S. PATENT DOCUMENTS

| | | | |
|---|---|---|---|
| 6,168,622 B1 | 1/2001 | Mazzocchi | |
| 6,231,573 B1* | 5/2001 | Amor et al. | 606/49 |
| 6,238,403 B1* | 5/2001 | Greene et al. | 606/108 |
| 6,270,523 B1 | 8/2001 | Herweck et al. | |
| 6,299,619 B1* | 10/2001 | Greene et al. | 606/108 |
| 6,309,367 B1 | 10/2001 | Boock | |
| 6,309,413 B1 | 10/2001 | Dereume et al. | |
| 6,331,191 B1 | 12/2001 | Chobotov | |
| 6,342,068 B1 | 1/2002 | Thompson | |
| 6,344,041 B1 | 2/2002 | Kupiecki et al. | |
| 6,344,048 B1 | 2/2002 | Chin et al. | |
| 6,346,117 B1 | 2/2002 | Greenhalgh | |
| 6,350,270 B1 | 2/2002 | Roue | |
| 6,375,668 B1 | 4/2002 | Gifford et al. | |
| 6,391,037 B1 | 5/2002 | Greenhalgh | |
| 6,409,749 B1 | 6/2002 | Maynard | |
| 6,428,558 B1 | 8/2002 | Jones et al. | |
| 6,440,098 B1* | 8/2002 | Luscher | 604/57 |
| 6,454,780 B1 | 9/2002 | Wallace | |
| 6,500,190 B2 | 12/2002 | Greene et al. | |
| 6,506,204 B2 | 1/2003 | Mazzocchi | |
| 6,527,790 B2* | 3/2003 | Chien et al. | 606/194 |
| 6,530,934 B1* | 3/2003 | Jacobsen et al. | 606/157 |
| 6,547,804 B2 | 4/2003 | Porter et al. | |
| 6,569,190 B2 | 5/2003 | Whalen et al. | |
| 6,585,748 B1 | 7/2003 | Jeffree | |
| 6,602,261 B2 | 8/2003 | Greene et al. | |
| 6,605,111 B2 | 8/2003 | Bose et al. | |
| 6,613,074 B1 | 9/2003 | Mitelberg et al. | |
| 6,626,928 B1 | 9/2003 | Raymond et al. | |
| 6,656,214 B1 | 12/2003 | Fogarty et al. | |
| 6,673,103 B1 | 1/2004 | Golds et al. | |
| 6,723,108 B1 | 4/2004 | Jones et al. | |
| 6,746,468 B1 | 6/2004 | Sepetka et al. | |
| 6,770,087 B2 | 8/2004 | Layne et al. | |
| 6,780,196 B2 | 8/2004 | Chin et al. | |
| 6,786,920 B2 | 9/2004 | Shannon et al. | |
| 6,790,225 B1 | 9/2004 | Shannon et al. | |
| 6,802,851 B2 | 10/2004 | Jones et al. | |
| 6,811,560 B2 | 11/2004 | Jones et al. | |
| 6,855,153 B2 | 2/2005 | Saadat | |
| 6,855,154 B2* | 2/2005 | Abdel-Gawwad | 606/200 |
| 6,958,061 B2 | 10/2005 | Truckai et al. | |
| 6,960,217 B2 | 11/2005 | Bolduc | |
| 6,979,344 B2 | 12/2005 | Jones et al. | |
| 7,029,487 B2 | 4/2006 | Greene et al. | |
| 7,052,513 B2 | 5/2006 | Thompson | |
| 7,070,609 B2 | 7/2006 | West | |
| 7,083,632 B2 | 8/2006 | Avellanet et al. | |
| 7,083,643 B2 | 8/2006 | Whalen et al. | |
| 7,153,323 B1 | 12/2006 | Teoh et al. | |
| 7,156,871 B2 | 1/2007 | Jones et al. | |
| 7,186,263 B2 | 3/2007 | Golds et al. | |
| 7,201,762 B2 | 4/2007 | Greene, Jr. et al. | |
| 7,211,109 B2 | 5/2007 | Thompson | |
| 7,229,461 B2 | 6/2007 | Chin et al. | |
| 7,303,571 B2 | 12/2007 | Makower et al. | |
| 7,306,622 B2 | 12/2007 | Jones et al. | |
| 7,306,624 B2 | 12/2007 | Yodfat et al. | |
| 7,491,214 B2 | 2/2009 | Greene et al. | |
| 7,520,893 B2 | 4/2009 | Rivelli | |
| 7,569,066 B2 | 8/2009 | Gerberding | |
| 7,753,931 B2 | 7/2010 | Diaz et al. | |
| 7,766,871 B2 | 8/2010 | Hirszowicz et al. | |
| 7,803,180 B2 | 9/2010 | Burpee et al. | |
| 7,806,857 B2 | 10/2010 | Khosravi et al. | |
| 2002/0042628 A1 | 4/2002 | Chin et al. | |
| 2002/0169473 A1 | 11/2002 | Sepetka et al. | |
| 2003/0009208 A1* | 1/2003 | Snyder et al. | 607/116 |
| 2003/0083676 A1 | 5/2003 | Wallace | |
| 2003/0093097 A1 | 5/2003 | Avellanet et al. | |
| 2003/0135264 A1 | 7/2003 | Whalen et al. | |
| 2003/0181927 A1 | 9/2003 | Wallace | |
| 2003/0187473 A1 | 10/2003 | Berenstein et al. | |
| 2003/0195553 A1 | 10/2003 | Wallace et al. | |
| 2004/0098027 A1 | 5/2004 | Teoh et al. | |
| 2004/0153025 A1* | 8/2004 | Seifert et al. | 604/19 |
| 2004/0158282 A1 | 8/2004 | Jones et al. | |
| 2004/0181253 A1 | 9/2004 | Sepetka et al. | |
| 2005/0021077 A1 | 1/2005 | Chin et al. | |
| 2005/0033349 A1 | 2/2005 | Jones et al. | |
| 2005/0043786 A1* | 2/2005 | Chu et al. | 623/1.42 |
| 2005/0267510 A1 | 12/2005 | Razack | |
| 2006/0052816 A1 | 3/2006 | Bates et al. | |
| 2006/0052821 A1* | 3/2006 | Abbott et al. | 606/213 |
| 2006/0058834 A1 | 3/2006 | Do et al. | |
| 2006/0079923 A1 | 4/2006 | Chhabra et al. | |
| 2006/0116709 A1 | 6/2006 | Sepetka et al. | |
| 2006/0116712 A1 | 6/2006 | Sepetka et al. | |
| 2006/0116713 A1* | 6/2006 | Sepetka et al. | 606/200 |
| 2006/0155323 A1 | 7/2006 | Porter et al. | |
| 2006/0206139 A1 | 9/2006 | Tekulve | |
| 2006/0235464 A1 | 10/2006 | Avellanet et al. | |
| 2006/0276831 A1 | 12/2006 | Porter et al. | |
| 2006/0292206 A1 | 12/2006 | Kim et al. | |
| 2007/0038288 A1 | 2/2007 | Lye et al. | |
| 2007/0050008 A1 | 3/2007 | Kim et al. | |
| 2007/0055355 A1 | 3/2007 | Kim et al. | |
| 2007/0078506 A1 | 4/2007 | Mccormick et al. | |
| 2007/0088387 A1 | 4/2007 | Eskridge et al. | |
| 2007/0106311 A1 | 5/2007 | Wallace et al. | |
| 2007/0150041 A1 | 6/2007 | Evans et al. | |
| 2007/0150045 A1 | 6/2007 | Ferrera | |
| 2007/0167747 A1 | 7/2007 | Borgert et al. | |
| 2007/0168011 A1 | 7/2007 | LaDuca et al. | |
| 2007/0173757 A1* | 7/2007 | Levine et al. | 604/95.04 |
| 2007/0207186 A1 | 9/2007 | Scanlon et al. | |
| 2007/0219578 A1* | 9/2007 | Solar et al. | 606/200 |
| 2007/0219610 A1 | 9/2007 | Israel | |
| 2007/0219619 A1 | 9/2007 | Dieck | |
| 2007/0239261 A1 | 10/2007 | Bose et al. | |
| 2007/0276469 A1 | 11/2007 | Tenne | |
| 2007/0276470 A1 | 11/2007 | Tenne | |
| 2008/0004653 A1 | 1/2008 | Sherman et al. | |
| 2008/0033341 A1 | 2/2008 | Grad | |
| 2008/0033480 A1 | 2/2008 | Hardert | |
| 2008/0039933 A1 | 2/2008 | Yodfat et al. | |
| 2008/0045996 A1 | 2/2008 | Makower et al. | |
| 2008/0097391 A1* | 4/2008 | Feinberg et al. | 604/523 |
| 2008/0114391 A1 | 5/2008 | Dieck et al. | |
| 2008/0114436 A1 | 5/2008 | Dieck et al. | |
| 2008/0147100 A1 | 6/2008 | Wallace | |
| 2008/0221554 A1 | 9/2008 | O'Connor | |
| 2008/0281350 A1* | 11/2008 | Sepetka et al. | 606/200 |
| 2008/0319521 A1 | 12/2008 | Norris et al. | |
| 2009/0012564 A1* | 1/2009 | Chirico et al. | 606/246 |
| 2009/0192536 A1 | 7/2009 | Berez et al. | |
| 2009/0198318 A1 | 8/2009 | Berez et al. | |
| 2009/0287291 A1 | 11/2009 | Becking et al. | |
| 2009/0287294 A1 | 11/2009 | Rosqueta et al. | |
| 2009/0299326 A1 | 12/2009 | Morsi | |
| 2009/0299448 A1 | 12/2009 | Timko et al. | |
| 2009/0318947 A1 | 12/2009 | Garcia et al. | |
| 2010/0004671 A1 | 1/2010 | Gerberding et al. | |
| 2010/0004726 A1 | 1/2010 | Hancock et al. | |
| 2010/0010624 A1 | 1/2010 | Berez et al. | |
| 2010/0030241 A1* | 2/2010 | Yeung et al. | 606/146 |
| 2010/0049165 A1* | 2/2010 | Sutherland et al. | 604/508 |
| 2010/0063531 A1 | 3/2010 | Rudakov et al. | |
| 2010/0069948 A1 | 3/2010 | Veznedaroglu et al. | |
| 2010/0094335 A1 | 4/2010 | Gerberding et al. | |
| 2010/0106240 A1 | 4/2010 | Duggal et al. | |
| 2010/0152828 A1 | 6/2010 | Pakbaz et al. | |
| 2010/0262124 A1 | 10/2010 | Hirszowicz et al. | |
| 2010/0274276 A1 | 10/2010 | Chow et al. | |
| 2010/0274346 A1 | 10/2010 | Chouinard et al. | |
| 2010/0280590 A1 | 11/2010 | Sun et al. | |
| 2012/0158034 A1* | 6/2012 | Wilson et al. | 606/192 |

\* cited by examiner

Fig. 12

ANEURYSM OCCLUSION BY ROTATIONAL DISPENSATION OF MASS

FEDERALLY SPONSORED RESEARCH

Not Applicable

SEQUENCE LISTING OR PROGRAM

Not Applicable

BACKGROUND

1. Field of Invention

This invention relates to treating aneurysms.

2. Review and Limitations of the Prior Art

An aneurysm is an abnormal localized bulging or ballooning of the wall of a blood vessel. A cerebral aneurysm is an abnormal bulging or ballooning of an intercerebral artery. The prevalence of cerebral aneurysms is in the range of 1-5%. According to the National Institute of Neurological Disorders and Stroke (NINDS) of NIH, the incidence of reported ruptured aneurysms is about 10 per 100,000 persons per year (about 27,000 per year in the U.S.). Approximately one third to one half of people who suffer a ruptured cerebral aneurysm die within one month and, among those who survive, approximately one half suffer significant deterioration of brain function. The vast majority of cerebral aneurysms form in the junction of arteries known as the Circle of Willis where arteries come together and from which these arteries send branches to different areas of the brain.

The most common methods of treating aneurysms are surgical clipping (placing a clamp on the aneurysm from outside the vessel) and endovascular coiling (inserting flexible coils into the aneurysm from inside the vessel). During the past three decades, there has been a general trend away from surgical clipping and toward less-invasive endovascular methods of treating aneurysms such as coiling. The limitations of surgical clipping include the risks of invasive surgery and difficulty accessing aneurysms in some areas. We will now discuss endovascular coiling in greater depth because the invention disclosed here is more similar to coiling than to clipping. The following are serious problems with endovascular coiling in the prior art that will be corrected by the present invention:

1. Limited Fill Volume Due to Resilient and Springy Coils

Endovascular coils in the prior art tend to be relatively resilient and springy. They are often metal. These qualities are needed in traditional coiling in order to create the surface tension between the coils and the aneurysm walls that holds the coils within the aneurysm sack. The coil loops do not form a solid mass within the aneurysm and would likely prolapse into the parent vessel if they were not resilient and springy. However, the resilient and springy nature of coils in the prior art limits the percentage of the aneurysm volume that can be filled by these coils. As these coils overlap in loops, there are often large gaps between them. Fill rates for the aneurysm sack volume can be as low as 25%-50%. Much of the volume of the aneurysm remains unfilled. As a result of these low fill rates, sometimes blood can continue to flow into the aneurysm and the aneurysm can continue to expand or even rupture.

2. Coil Prolapse Due to Randomness of Coil Loop Directions

In deployment of endovascular coils in the prior art, the directionality of looping within the aneurysm during coiling is constantly changing, highly variable, and somewhat random in nature. Although a talented and experienced practitioner can exert some control over the changing directionality of coil looping by manipulating the device from outside the patient's body, it can be laborious for the practitioner to constantly work at avoiding having the loops turn in a direction that could prolapse into the parent vessel. Coil loops that prolapse into the parent vessel can block blood flow in real time. Prolapsed coils can also cause embolization or stoke in the future.

3. Long Procedure Time Due to Randomness of Coil Loop Directions

In addition to the possibility of coil prolapse into the parent vessel due to the randomness of changing loop directionality in traditional endovascular coiling, this randomness also makes the procedure time consuming. It can be very time-consuming for a practitioner to gradually snake coils around the aneurysm, one loop at a time, in different directions. This is especially true when multiple coils are used or when coils with different characteristics are used at different stages in the procedure.

For these reasons, despite significant progress in surgical clipping and endovascular coiling during the past two decades, there remains a significant unmet clinical need for development of a new option to treat cerebral aneurysms that can address these four problems. The invention that we will now disclose is a novel option for treating cerebral aneurysms that can address these problems and meet this unmet clinical need.

SUMMARY AND ADVANTAGES OF THIS INVENTION

This invention is a device for occluding an aneurysm comprising: a rotating member that is inserted into, and then rotated within, the aneurysm; and one or more fill members that are dispensed outwards from one or more openings in the rotating member toward the aneurysm walls. Coordination of the rate of rotation of the rotating member with the rate at which the one or more fill members are dispensed from the rotating member can create a densely-packed spiraling mass that fills a higher percentage of the volume of the aneurysm interior than is possible with deployment of coils in the less-directed, relatively-random manner used in the prior art. This invention corrects the problems with coils in the prior art that were just discussed in the previous section, as follows:

1. Corrects Limited Fill Volume Due to Resilient and Springy Coils

Rotational dispensation of mass from a central rotating member, as disclosed in this present invention, corrects this problem. With rotational dispensation of mass from a central rotating member, the longitudinal fill members do not have to be resilient and springy. They can be held within the aneurysm sack due to self-adhesion in a manner that is not possible with traditional coils and can be densely packed into a solid, spiraling mass within the aneurysm. This can enable filling a much higher volume of the aneurysm, which can reduce the chances that the aneurysm will continue to expand or rupture.

2. Corrects Coil Prolapse Due to Randomness of Coil Loop Directions

Rotational dispensation of mass from a central rotating member, as disclosed in this present invention, corrects this problem. In this invention, the directionality of fill member spiraling is primarily constrained to one or more planes that are substantially parallel to the longitudinal axis of the parent vessel. Generally these planes are parallel with the neck of the aneurysm. In contrast to current coiling methods, this avoids coils that can loop in planes that are perpendicular to the neck of the aneurysm. In this manner, this invention avoids loops 3. Corrects Long Procedure Time Due to Randomness of Coil Loop Directions Rotational dispensation of mass from a central rotating member, as disclosed in this present invention, corrects this problem. The simple rotational process can quickly and efficiently fill the entire radial space of an aneurysm with accumulated mass. There is no need to manage partially-random changes in loop direction to avoid coils prolapsing into the parent vessel. Ideally, the practitioner will be able to just: insert this device into the aneurysm; activate the rotational dispensation of mass until the aneurysm is appropriately filled (either based on imaging or automatic shut off); and then detach and withdraw the catheter. In this manner, this invention can reduce operating time, thereby reducing risk and expense for the patent and the health care system.

DETAILED DESCRIPTION OF THE FIGURES

These figures show some examples of the ways in which this invention may be embodied. However, they are only examples and do not limit the full generalizability of the claims.

Figure 1:
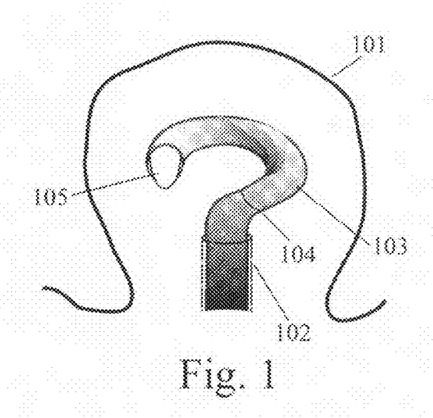
FIGS. 1 through 4 show one embodiment of this invention that features a rotating hollow spiral member that is inserted onto, and rotated within, an aneurysm in order to deploy a soft and flexible longitudinal fill member so as to therapeutically occlude the aneurysm.

FIGS. 1 through 4 show one embodiment of this invention that features a rotating hollow spiral member that is inserted into, and rotated within, an aneurysm in order to deploy a soft and flexible longitudinal fill member so as to therapeutically occlude the aneurysm. FIGS. 1 through 4 show this embodiment, from a lateral perspective within the aneurysm, in four different stages of deployment. FIG. 1 shows this embodiment in the first stage of deployment, wherein hollow spiral member 103, at the distal end of a tube inside catheter 102, has been inserted into the center of aneurysm 101. In this example, catheter 102 protects blood vessels along the route from the point entry of the catheter into the body from potential harm from rotation of the tube ending in hollow spiral member 103. In another example, catheter 102 may be omitted if rotation of the tube would not be harmful to blood vessels along this route.

In the embodiment of this invention that is shown in FIG. 1, there is one opening at the distal end of hollow spiral member 103. A soft and flexible longitudinal fill member, 105, exits hollow spiral member 103 into aneurysm 101 through this opening. In FIG. 1, the tip of longitudinal fill member 105 can be seen just beginning to protrude out of this opening at the end of hollow spiral member 103. In another example, there may be more than one opening and more than one fill member simultaneously exiting a hollow rotating member. For example, there could be a rotating member with a double spiral arm, like a spiral galaxy, with openings at the end of each arm. This latter design would deploy two longitudinal fill members in a symmetric manner as the double spiral rotates. In various examples, the rotating member inserted into the aneurysm may have a shape selected from the group consisting of: spiral, partial spiral, double spiral, or conchshell design; cylinder with rounded ends; and sphere, ellipsoid, or ovaloid. In various examples, hollow spiral 103 may be made from one or more materials selected from the group consisting of: ethylene propylene diene monomer (EPDM), latex, silicone, polyvinyl chloride, and polyurethane.

In this example, longitudinal fill member 105 has a flexible metal wire core that is surrounded by a thick and soft flexible foam layer. In various examples, the configuration of longitudinal fill member may be selected from the group consisting of: a plain coil or other flexible metal member 105; a longitudinal member with a flexible metal core and an outer layer made from flexible foam, sponge, or biological material; a flow of liquid or gel that solidifies shortly after exiting the rotating member; a longitudinal foam, sponge, or biological outer layer; and a chain of fill members connected by a central metal, polymer, or fabric strand. In various examples, the longitudinal fill member may be made from one or more materials selected from the group consisting of: platinum or platinum alloy; collagen or collagen polymer; hydrophilic acrylic polymer, tricellulose acetate polymer, fibrin polymer, bioabsorbable polymer, or other biocompatible polymer; and polyester, polyethylene, polypropylene, polytetrafluorethylene, or polytetrafluoroethene. In various examples, the longitudinal fill member may have a cross-sectional diameter in the range of 50 micrometers to about 2000 micrometers. In an example, the spiral rotating member, a fill member, or both, may be radio-opaque to help the operator see it during deployment within the body.

In this example, there is a severable cross-section 104 at one location between the hollow spiral 103 and the main body of the tube with which spiral 103 is integrated. This severable cross-section 104 may be severed, such as by electricity-induced melting or mechanical cutting action, in order to detach hollow spiral 103 from the main body of the tube and catheter 102 after successful deployment of the longitudinal fill member 105. Such detachment, as shown in a subsequent figure of this example, leaves hollow spiral member 103 as part of the occluding mass in the aneurysm when catheter 102 is removed from the body. In another example, hollow spiral member 103 may be disengaged from the occluding mass and removed from the body at the same time that the main body of the tube and catheter 102 are removed from the body. In this latter case, severable cross-section 104 is not required; instead hollow spiral member 103 is slowly turned clockwise and extracted from the mass of longitudinal fill member 105.

Figure 2:
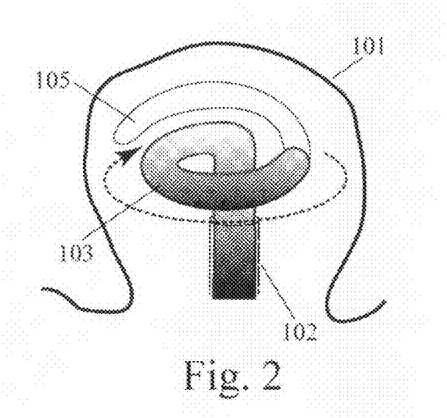

FIG. 2 shows a second stage of deployment of the embodiment of this invention that was introduced in FIG. 1. In FIG. 2, hollow spiral member 103 has begun to rotate within aneurysm 101 and a portion of longitudinal fill member 105 has been dispensed out of the opening at the end of spiral member 103. In this example, longitudinal fill member 105 is pushed out of the opening at the end of hollow spiral member 103 by operator action that occurs at the proximal end of the tube, outside the patient's body. This operator action may be manual, automated, or a mixture thereof.

In this example, hollow spiral member 103 is actively rotated by active rotation of the tube with which it is integrated. This tube is actively rotated at its proximal end, outside the body, by either manual or automatic action. In another example, hollow spiral member 103 could be connected to the tube with a rotatable joint, such as with ball bearings. In this latter case, the spiral member may rotate passively (rather than actively) in counter-response to pressure from fill member 105 as fill member 105 exits the opening and comes into contact with the wall of aneurysm 101, the portion of fill member 105 that is already in the aneurysm, or both. In an example, the surface of longitudinal fill member 105 may stick to itself, but not to the surface of rotating member 103. The ability of longitudinal member to stick to itself could help to avoid prolapse of the accumulated spiraling mass of longitudinal member 105 through the neck of the aneurysm into the parent vessel of the aneurysm.

In this example, longitudinal fill member 105 exits hollow spiral 103 in a direction that is substantially perpendicular to, and radiating outwards from, the rotational axis of spiral member 103. Perpendicular dispensing of the longitudinal member into the aneurysm, combined with rotation of the spiral member, helps to configure the longitudinal member into a densely-packed disk or sphere, comprised of a winding spiral, with a maximum central diameter that is roughly perpendicular to the rotational axis of rotating member 103. When the rotating member is inserted into the aneurysm at an angle that is roughly perpendicular to the plane of the aneurysm neck, then this densely-packed disk or sphere is well-configured to occlude the aneurysm without prolapsing into the parent vessel. If the aneurysm is in a location wherein it is difficult to insert the rotating member at an angle that is roughly perpendicular to the plane of the aneurysm neck using a straight catheter, then a catheter may be used with a permanent curve at its distal end or a catheter may be used with a steering mechanism at its distal end to create such a curve in vivo.

In an example, the rotating member, such as hollow spiral member 103, may be inserted into, and then subsequently rotated within, aneurysm 101. In an example, the rotating member may rotate around an axis that is substantially perpendicular to the longitudinal axis of the parent vessel from which the aneurysm sac extends. In an example, this rotational axis may also be substantially central to the aneurysm sac. In an example, one or more fill members, such as fill member 105, may be dispensed outwards from the rotating member toward the aneurysm walls as the rotating member rotates. In an example, the one or more fill members may be dispensed outwards from one or more holes in the rotating member. In an example, the one or more fill members may accumulate within the aneurysm in a spiraling mass as they are dispensed. In an example, the spirals in the mass may form in one or more planes that are substantially parallel to the longitudinal axis of the parent vessel from which the aneurysm sac extends.

Figure 3:
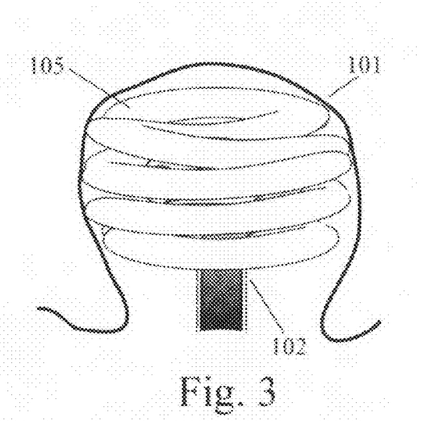

FIG. 3 shows this same embodiment in a third stage of deployment. In FIG. 3, hollow spiral member 103 has now made several rotations while dispensing longitudinal fill member 105 out of the opening at its distal end. The combination of the radial deployment (outward from the rotational axis of rotating spiral 103) and the rotation of hollow spiral member 103 have combined to deploy longitudinal fill member into a closely-packed spiraling mass that spans the circumference, and fills the interior, of aneurysm 101. When the rate of rotation of rotating member 103 is properly coordinated with the rate at which longitudinal member 105 is dispensed out from the opening in the rotating member, then the result is a densely-wound spiraling mass that can fill a greater percentage of the volume of the aneurysm than is accomplished with current methods of aneurysm occlusion using coils in a less-directed, relatively-random manner.

Figure 4:
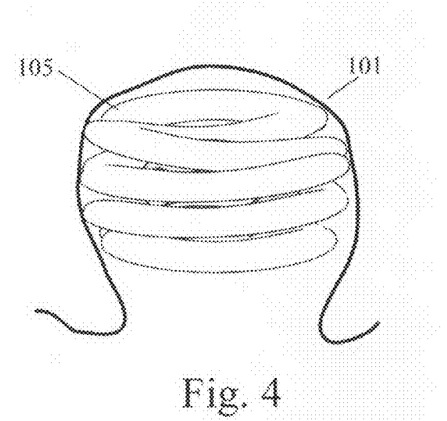

FIG. 4 shows the final stage of deployment of this embodiment of this invention. In FIG. 4, the central area of the aneurysm has been densely-filled with overlapping spirals of longitudinal fill member 105. Catheter 102 has now been removed from the body. The mass left behind in the aneurysm therapeutically occludes the aneurysm so that it is less likely to burst and so that blood vessel wall tissue can form across the neck of the aneurysm. In this example, a single longitudinal fill member 105 is used. In another example, multiple longitudinal fill members may be used—ideally with a surface that self-adheres so as to form a densely-packed and self-containing mass that does not prolapse into the parent vessel. In another example, multiple fill members may be deployed within an expandable net or mesh so that they are held together and do not prolapse into the parent vessel, without the need for self-adhesion.

In the final stage of the embodiment that is shown in FIG. 4, the severable cross-section 104 between hollow spiral member 103 and the tube with which it was integrated has been severed, leaving the spiral member behind within the spiraling mass of longitudinal fill member 105 when catheter 102 is withdrawn from the body. Severing the cross-section can be accomplished by melting of the cross-section with a modest electrical pulse or by a mechanical cutting mechanism. In another example, hollow spiral member 103 may not be detached from the tube. In this latter case, hollow spiral member 103 may be gently removed from the spiraling mass of longitudinal fill member 105 by slow, clockwise rotation accompanied by gentle pulling motion.

FIGS. 5 through 8 show a second embodiment of this invention that also features a rotating hollow spiral member that is inserted into, and rotated within, an aneurysm, but now involves deployment of a metal coil 501 to therapeutically occlude the aneurysm. FIGS. 5 through 8 show this embodiment, from a lateral perspective within the aneurysm, in four different stages of deployment.

Figure 5:
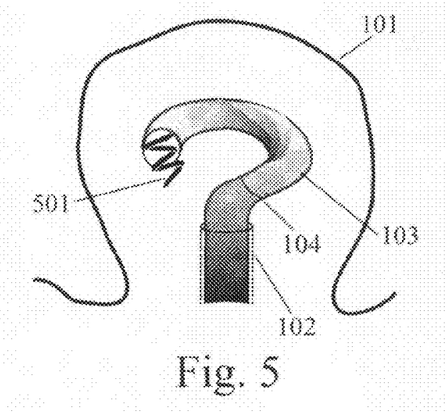
FIGS. 5 through 8 show a second embodiment of the invention that also features a rotating hollow spiral member that is inserted into, and rotated within, an aneurysm, but now involves deployment of a metal coil 501 to therapeutically occlude the aneurysm.

FIG. 5 shows this second embodiment in a first stage of deployment, wherein hollow spiral member 103 at the distal end of a tube inside catheter 102 has been inserted into aneurysm 101. In this second embodiment a flexible coil 501 exits hollow spiral member 103 into aneurysm 101 through an opening at the end of hollow spiral 103. In FIG. 5, the tip of coil 501 can be seen just beginning to protrude out of this opening at the end of hollow spiral member 103. In another example, there may be more than one opening and more than one coil simultaneously exiting a hollow rotating member. For example, there could be a rotating member with a double spiral arm, like a spiral galaxy, with openings at the end of each arm. This latter design would deploy two coils in a symmetric manner as the double spiral rotates. In various examples, the rotating member inserted into the aneurysm may have a shape selected from the group consisting of: spiral, partial spiral, double spiral, or conch-shell design; cylinder with rounded ends; and sphere, ellipsoid, or ovaloid. In various examples, rotating spiral member 103 may be made from one or more materials selected from the group consisting of: ethylene propylene diene monomer (EPDM), latex, silicone, polyvinyl chloride, and polyurethane. The coil may be made from platinum, a platinum allow, or a polymer.

Figure 6:
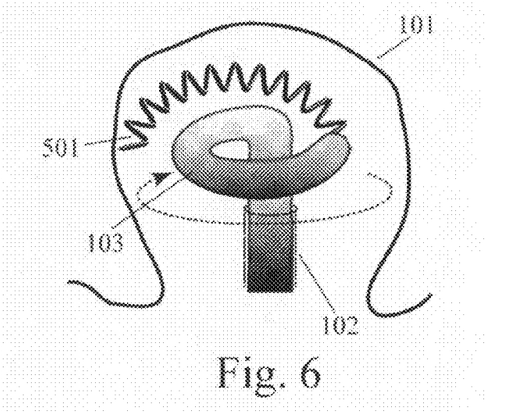

FIG. 6 shows a second stage of deployment of this embodiment in which hollow spiral member 103 has begun to rotate within aneurysm 101 and a portion of coil 501 has been dispensed out of the opening at the end of spiral member 103. In this example, coil 501 is pushed out of the opening at the end of hollow spiral member 103 by operator action that occurs at the proximal end of the tube, outside the patient's body. This operator action may be manual, automated, or a mixture thereof.

In this example, hollow spiral member 103 is actively rotated by active rotation of the tube with which it is integrated. This tube is actively rotated at its proximal end, outside the body, by either manual or automatic action. In another example, hollow spiral member 103 could be connected to the tube with a rotatable joint, such as with ball bearings. In this latter case, the spiral member may rotate passively (rather than actively) in counter-response to pressure from coil 501 as coil 501 exits the opening and comes into contact with the wall of aneurysm 101, the portion of coil 501 that is already in the aneurysm, or both.

In this example, coil 501 exits rotating spiral member 103 in a manner that is roughly perpendicular to, and radiating outwards from, the rotational axis of spiral member 103. Perpendicular dispensing of the longitudinal member into the aneurysm, combined with rotation of the spiral member, helps to configure the longitudinal member into a densely-packed disk or sphere, comprised of a winding spiral, with a maximum central diameter that is roughly perpendicular to the rotational axis of rotating member 103. When the rotating member is inserted into the aneurysm at an angle that is roughly perpendicular to the plane of the aneurysm neck, then this densely-packed disk or sphere is well-configured to occlude the aneurysm without prolapsing into the parent vessel. If the aneurysm is in a location wherein it is difficult to insert the rotating member at an angle that is roughly perpendicular to the plane of the aneurysm neck using a straight catheter, then a catheter may be used with a permanent curve at its distal end or a catheter may be used with a steering mechanism at its distal end to create such a curve in vivo.

Figure 7:
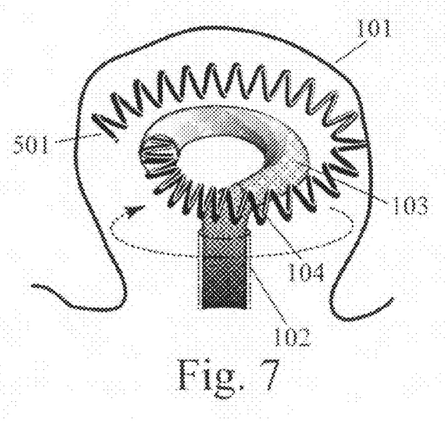

FIG. 7 shows this coil embodiment of the invention in a third stage of deployment. In FIG. 7, hollow spiral member 103 has now made several rotations while dispensing coil 501 out of the opening at its distal end. The combination of the radial deployment (outward from the rotational axis of rotating spiral 103) and the rotation of hollow spiral member 103 have combined to deploy coil into a closely packed spiraling mass that spans the circumference, and fills the interior, of aneurysm 101. When the rate of rotation of rotating member 103 is properly coordinated with the rate at which longitudinal member 501 is dispensed out from the opening in the rotating member, then the result is a densely-wound spiraling mass that can fill a greater percentage of the volume of the aneurysm interior than is accomplished with current methods of aneurysm occlusion using coils in a less-directed, relatively-random manner.

Figure 8:
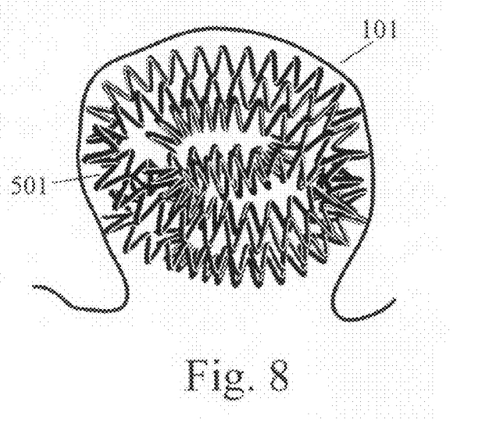

FIG. 8 shows the final stage of deployment of this coil embodiment. In FIG. 8, the central area of the aneurysm has been densely-filled with overlapping spirals of coil 501 and catheter 102 has been removed from the body. The mass left behind in the aneurysm therapeutically occludes the aneurysm so that it is less likely to burst and so that blood vessel wall tissue can form across the neck of the aneurysm. In this example, a single longitudinal coil 501 is used. In another example, multiple coils may be used. In the final stage of the embodiment that is shown in FIG. 8, hollow spiral member 103 has been gently removed from the spiraling mass of coil 501 by slow, clockwise rotation accompanied by gentle pulling motion.

Figure 9:
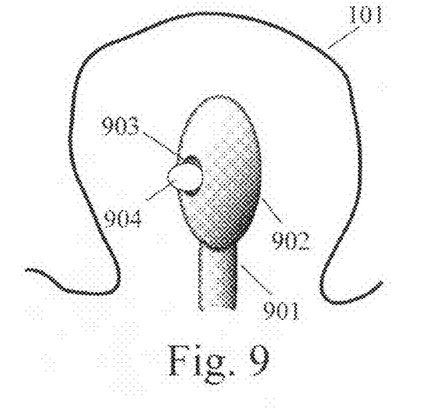
FIGS. 9 through 12 show a third embodiment of this invention that features a rotating hollow ellipsoid that is inserted into, and rotated within, an aneurysm, to deploy a longitudinal fill member out of opening in order to therapeutically occlude the aneurysm.

FIGS. 9 through 12 show a third embodiment of this invention that features a rotating hollow elipsoid 902 that is inserted into, and rotated within, aneurysm 101, to deploy a longitudinal fill member 904 out of opening 903 in order to therapeutically occlude aneurysm 101. FIGS. 9 through 12 show this embodiment, from a lateral perspective within the aneurysm, in four different stages of deployment. In FIG. 9, the tip of longitudinal fill member 904 can be seen just beginning to protrude out of this opening in hollow elipsoid 902. In another example, there may be more than one opening. In various examples, hollow elipsoid 902 may be made from one or more materials selected from the group consisting of: ethylene propylene diene monomer (EPDM), latex, silicone, polyvinyl chloride, and polyurethane.

In this example, longitudinal fill member 904 has a flexible metal wire core that is surrounded by a thick and soft flexible foam layer. In various other examples, the configuration of longitudinal fill member may be selected from the group consisting of: a plain coil or other flexible metal member; a longitudinal member with a flexible metal core and an outer layer made from flexible foam, sponge, or biological material; a flow of liquid or gel that solidifies shortly after exiting the rotating member; a longitudinal foam, sponge, or biological outer layer; and a chain of fill members connected by a central metal, polymer, or fabric strand. In various examples, the longitudinal fill member may be made from one or more materials selected from the group consisting of: platinum or platinum alloy; collagen or collagen polymer; hydrophilic acrylic polymer, tricellulose acetate polymer, fibrin polymer, bioabsorbable polymer, or other biocompatible polymer; and polyester, polyethylene, polypropylene, polytetrafluorethylene, or polytetrafluoroethene. In various examples, the longitudinal fill member may have a cross-sectional diameter in the range of 50 micrometers to about 2000 micrometers. In an example, the rotating elipsoid, fill member, or both, may be radio-opaque to help the operator see it during deployment within the body.

In this example, hollow elipsoid 902 is detached from tube 901 by electricity-induced melting or by mechanical cutting action after successful deployment of the longitudinal fill member. Such detachment, as shown in a subsequent figure of this example, leaves the hollow elipsoid as part of the occluding mass in the aneurysm when tube 901 is removed from the body. In another example, hollow elipsoid 902 may remain connected to tube 901. In this latter case, the elipsoid may be disengaged from the occluding mass and removed by gently pulling it out.

Figure 10:
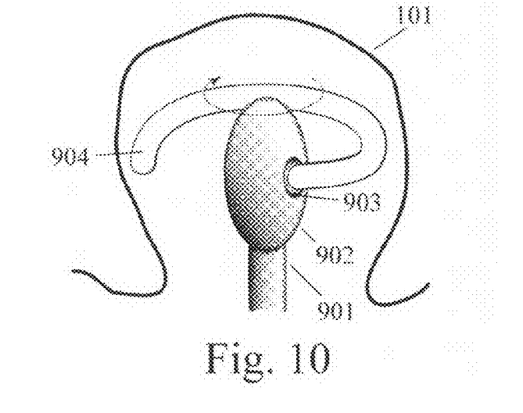

FIG. 10 shows a second stage of deployment of this embodiment in which hollow elipsoid 902 has begun to rotate within aneurysm 101 and a portion of longitudinal fill member 904 has been dispensed out of the opening in elipsoid 902. In this example, longitudinal fill member 904 is pushed out of the opening in hollow elipsoid 902 by operator action that occurs at the proximal end of the tube, outside the patient's body. This operator action may be manual, automated, or a mixture thereof.

In this example, hollow elipsoid 902 is actively rotated by active rotation of the tube 901 with which it is integrated. This tube is actively rotated at its proximal end, outside the body, by either manual or automatic action. In another example, hollow elipsoid 902 could be connected with tube 901 with a rotatable joint, such as with ball bearings. In this latter case, the elipsoid may rotate passively (rather than actively) in counter-response to pressure from fill member 904 as fill member 904 exits the opening and comes into contact with the wall of aneurysm 101, the portion fill member 904 that is already in the aneurysm, or both. In an example, the surface of longitudinal fill member 904 may stick to itself, but not to the surface of elipsoid 902. The ability of longitudinal member to stick to itself could help to avoid prolapse of the accumulated mass of longitudinal member 904 through the neck of the aneurysm into the parent vessel of the aneurysm.

In this example, longitudinal fill member 904 exits hollow elipsoid 902 in a manner that is roughly perpendicular to, and radiating outwards from, the rotational axis of elipsoid 902.

Perpendicular dispensing of the longitudinal member into the aneurysm, combined with rotation of the elipsoid, helps to configure the longitudinal member into a densely-packed disk or sphere, comprised of a winding spiral, with a maximum central diameter that is roughly perpendicular to the rotational axis of rotating elipsoid 902. When rotating elipsoid 902 is inserted into aneurysm at an angle that is roughly perpendicular to the plane of the neck, then this densely-packed disk or sphere is well-configured to occlude the aneurysm without prolapsing into the parent vessel. If the aneurysm is in a location wherein it is difficult to insert the rotating elipsoid at an angle that is roughly perpendicular to the plane of the aneurysm neck using straight tube 901, then a tube may be used with a permanent curve at its distal end or a tube may be used with a steering mechanism at its distal end to create such a curve in vivo.

Figure 11:
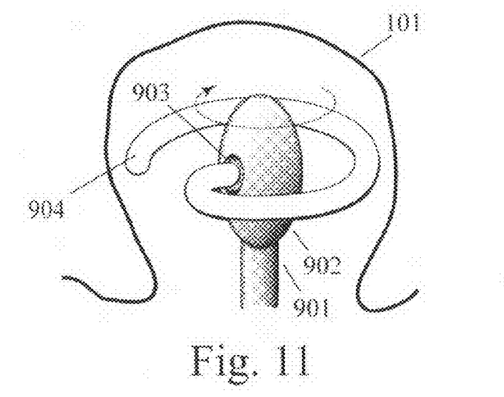

FIG. 11 shows this embodiment in a third stage of deployment in which elipsoid 902 has now made several rotations while dispensing longitudinal fill member 904 out of its opening. The combination of the radial deployment (outward from the rotational axis of rotating elipsoid 902) and the rotation of elipsoid 902 have combined to deploy longitudinal fill member 904 into a closely packed spiraling mass that spans the circumference, and fills the interior, of aneurysm 101. When the rate of rotation of rotating elipsoid 902 is properly coordinated with the rate at which longitudinal member 904 is dispensed out from the opening in the rotating member, then the result is a densely-wound spiraling mass that can fill a greater percentage of the volume of the aneurysm than is accomplished with current methods of aneurysm occlusion using coils in a less-directed, relatively-random manner.

Figure 12:
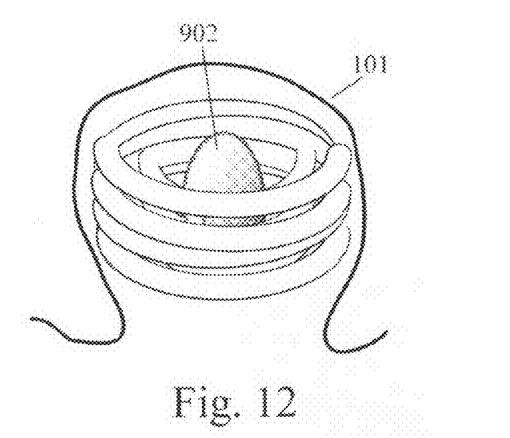

FIG. 12 shows the final stage of deployment of this embodiment in which the central area of the aneurysm has been densely-filled with overlapping spirals of longitudinal fill member 904 and in which tube 901 has been removed from the body. The mass left behind in the aneurysm therapeutically occludes the aneurysm so that it is less likely to burst and so that blood vessel wall tissue can form across the neck of the aneurysm. In this example, a single longitudinal fill member 904 was used. In another example, multiple longitudinal fill members may be used—ideally with a surface that self-adheres so as to form a densely-packed and self-containing spiraling mass that does not prolapse into the parent vessel. In another example, multiple fill members may be deployed within an expandable net or mesh so that they are held together and do not prolapse into the parent vessel, without the need for self-adhesion.

In the final stage of the embodiment that is shown in FIG. 12, hollow elipsoid 902 has been detached from tube 901, such as by melting or mechanical cutting action, leaving the elipsoid behind within the spiraling mass of longitudinal fill member 904 when tube 901 is withdrawn from the body. In another example, hollow elipsoid 902 may not be detached from tube 901. In this latter case, hollow elipsoid 902 may be gently removed from the spiraling mass by pulling slowly as tube 901 is removed.

I claim:

1. A device for occluding an aneurysm comprising,
    a rotating member with an arcuate distal portion, wherein the distal portion is configured to be inserted into and rotated within an aneurysm sac, wherein the distal portion has a spiral shape prior to being inserted into the aneurysm sac, wherein the rotating member has a rotational axis, wherein the distal portion further comprises at least one hole, wherein the rotating member further comprises a severable cross-section, and wherein severing the cross-section detaches the distal portion from the rest of the rotating member; and
    one or more fill members that are dispensed outwards from the at least one hole in the rotating member as the rotating member rotates within the aneurysm sac, wherein the one or more fill members exit the at least one hole in a direction that is substantially perpendicular to the rotational axis of the rotating member, wherein the one or more fill members form a spiral with at least one loop which completely encircles the rotational axis of the rotating member as the rotating member rotates and dispenses the one or more fill members within the aneurysm sac, and wherein the cross-section is severed after the one or more fill members have been dispensed from the at least one hole.

2. The device in claim 1 wherein: a loop plane is defined as the plane which is perpendicular to the rotational axis of the rotating member which most closely captures the at least one loop; and wherein the loop plane intersects the rotational axis of the rotating member at a location which is proximal to the distal end of the rotating member as the rotating member rotates and dispenses the one or more fill members.

3. The device in claim 1 wherein the one or more fill members are selected from the group consisting of: longitudinal coil, wire, or other flexible metal member; longitudinal fill member with a flexible metal core and soft outer layer made from foam, sponge, polymer, or biological material; flow of liquid or gel that solidifies soon after exiting the rotating member; plongitudinal foam, sponge, polymer, or biological member; and chain or series of filler members connected by a wire, fiber, or strand.

4. A device for occluding an aneurysm comprising,
    a rotating member with an arcuate distal portion, wherein the distal portion is configured to be inserted into and rotated within an aneurysm sac, wherein the distal portion has a spiral shape prior to being inserted into the aneurysm sac, wherein the rotating member has a rotational axis, wherein the distal portion further comprises at least one hole, wherein the rotating member further comprises a severable cross-section, and wherein severing the cross-section detaches the distal portion from the rest of the rotating member;
    one or more fill members that are dispensed outwards from the at least one hole in the rotating member as the rotating member rotates within the aneurysm sac, wherein the one or more fill members exit the at least one hole in a direction that is substantially perpendicular to the rotational axis of the rotating member, wherein the one or more fill members form a spiral as the rotating member rotates and dispenses the one or more fill members within the aneurysm sac, wherein this spiral further comprises a first loop which completely encircles the rotational axis of the rotating member, wherein this spiral further comprises a second loop which completely encircles the rotational axis of the rotating member, wherein the second loop is contiguous to the first loop, wherein a first loop plane is defined as the plane which most closely captures the first loop, wherein a second loop plane is defined as the plane which most closely captures the second loop, where the first loop plane and the second loop plane are each substantially perpendicular to the rotational axis of the rotating member, and wherein the cross-section is severed after the one or more fill members have been dispensed from the at least one hole.

5. The device in claim 4 wherein the one or more fill members are selected from the group consisting of: longitudinal coil, wire, or other flexible metal member; longitudinal fill member with a flexible metal core and soft outer layer made from foam, sponge, polymer, or biological material; flow of liquid or gel that solidifies soon after exiting the rotating member; plongitudinal foam, sponge, polymer, or biological member; and chain or series of filler members connected by a wire, fiber, or strand.

\* \* \* \* \*